US00PP25746P3

(12) United States Plant Patent
Clark et al.

(10) Patent No.: US PP25,746 P3
(45) Date of Patent: Jul. 28, 2015

(54) GRAPE PLANT NAMED 'GRATITUDE'

(50) Latin Name: ***Vitis labrusca* L.×*Vitis Vinifera* L.**
Varietal Denomination: Gratitude

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 178 days.

(21) Appl. No.: 13/987,496

(22) Filed: Jul. 31, 2013

(65) Prior Publication Data

US 2015/0040277 P1 Feb. 5, 2015

(51) Int. Cl.
*A01H 5/00* (2006.01)

(52) U.S. Cl.
USPC ..... Plt./207

(58) Field of Classification Search
USPC ..... Plt./207
See application file for complete search history.

(56) References Cited

U.S. PATENT DOCUMENTS

PP13,309 P2 12/2002 Clark
2012/0297511 P1 11/2012 Clark et al.

OTHER PUBLICATIONS

Clark, J.R. et al., "'Faith', 'Gratitude', 'Hope', and 'Joy' Seedless Table Grapes," (2013) HortScience 48(7):913-919.
Clark, J.R. et al., "'Osage' Thornless Blackberry and 'Hope', 'Faith', 'Joy', and 'Gratitude' Table Grapes," (2013) SR-ASHS Annual conference HortScience 48(9) (Supplement)—2013 SR-ASHS Annual Meeting, p. S33.
U.S. Appl. No. 13/987,494, filed Jul. 31, 2013.
U.S. Appl. No. 13/987,497, filed Jul. 31, 2013.
U.S. Appl. No. 13/987,501, filed Jul. 31, 2013.

*Primary Examiner* — Annette Para
(74) *Attorney, Agent, or Firm* — Andrus Intellectual Property Law, LLP

(57) ABSTRACT

Description and specifications of a new and distinct grapevine cultivar named 'Gratitude' which originated from a hand-pollinated cross of A-1925 (non-patented, non-released breeding genotype; female)×A-1581 (non-patented, non-released breeding genotype; male). This new grapevine cultivar can be distinguished by its seedless, green, crisp berries with neutral flavor and resists cracking from rainfall at maturity. The fruit grows in large tight clusters, the vines have medium vigor, and the plants are healthy.

3 Drawing Sheets

Latin name: *Vitis labrusca* L.×*Vitis vinifera* L.
Varietal denomination: 'Gratitude'.

BACKGROUND

The new and distinct cultivar of grape named 'Gratitude' is described herein. The new cultivar originated from a hand-pollinated cross of A-1925 (female parent) and A-1581 (male parent) made in 1991. The seedlings fruited in the summer of 1992 in a vineyard near Clarksville, Ark. and one was selected for its seedless, green, crisp berries with neutral flavor. The fruit grows in large tight clusters, the vines have medium vigor and the plants are healthy.

SUMMARY OF THE INVENTION

The new and distinct cultivar of grapevine originated from a hand-pollinated cross of A-1925 (non-patented, non-released genotype; female parent)×A-1581 (non-patented, non-released breeding genotype; male parent) made in 1991 near Clarksville, Ark. The instant cultivar is a hybrid of *Vitis labrusca* L. and *Vitis vinifera* L. The seeds resulting from this controlled hybridization were germinated in a greenhouse during the winter of 1991-92. Resulting seedlings were planted in the spring of 1992 in a vineyard near Clarksville, Ark. The seedlings fruited in the summer of 1994 and one seedling, designated Arkansas Selection 2505, was selected for its seedless, green, crisp berries with neutral flavor and resistance to fruit cracking in rainfall at maturity. The fruit grows in large tight clusters, the vines have medium vigor and the plants are healthy.

During late 1994 and early 1995, the original plant selection was propagated asexually at the above-noted location, by rooting hardwood cuttings and a test planting of three vines was established. In all propagations hardwood cuttings were used and the instant cultivar rooted readily from hardwood cuttings. All propagules (resulting plants) of the instant cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have medium vigor, with a procumbent growth habit characteristic of *V. labrusca*. It has produced well as own-rooted plants in all testing and has not been evaluated on any rootstocks. Hardiness of the vines has been very good, although slight winter injury has occurred on the vines when winter lows of 5° F. occurred but injury was not seen at winter temperatures above this level.

The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). Fungal diseases can be controlled by the use of available fungicides.

The new cultivar ripens its fruit in the late season, from August 19-28. The fruit is green in color at early maturity. It is evenly colored within the cluster. The fruit shape is elongated oval. Fruit skins are medium-thick and adhere to the flesh (has a non-slipskin texture). The berries are medium (ca. 3.6 g). The flavor is neutral in character. Solids concentration of the juice at fruit maturity averages 19% with medium acidity. The fruit is of the stenospermocarpic type of seedlessness and usually contains no seed traces. Fruit clusters, borne usually one to two per shoot, are large and tightly filled with an average weight of 516 g. The fruit clusters are considered large in size, good for commercial markets, and the variety is also intended for home garden planting.

The new cultivar has been named the 'Gratitude' cultivar.

BRIEF DESCRIPTION OF THE PHOTOGRAPHS

The accompanying photographs show typical specimens of the new variety at eight years of age in color as nearly true as it is reasonably possible to make in a color illustration of this character.

DETAILED DESCRIPTION OF THE NEW CULTIVAR

Figure 1:
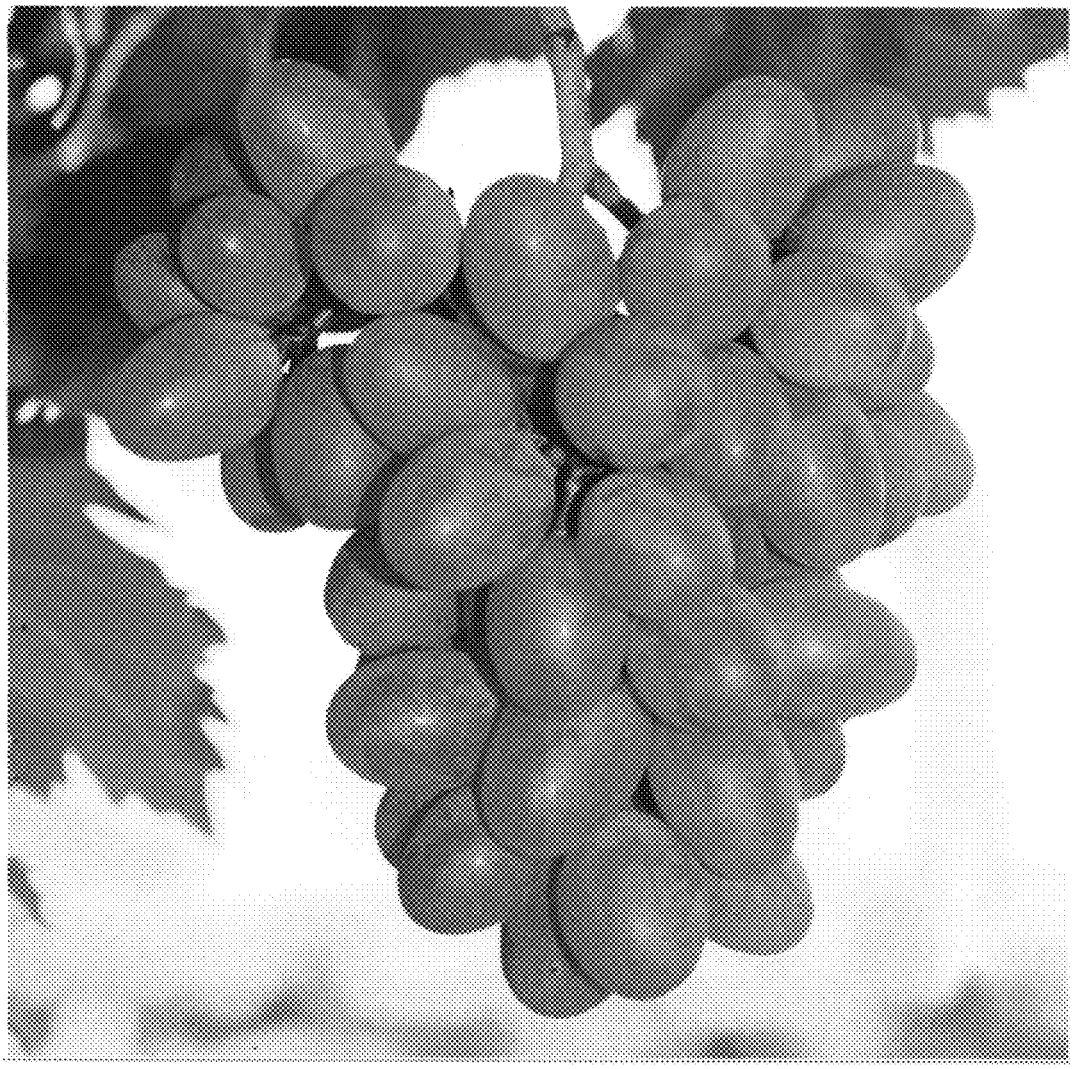
FIG. 1 is a photograph showing typical specimens of the fruit.
Figure 2:
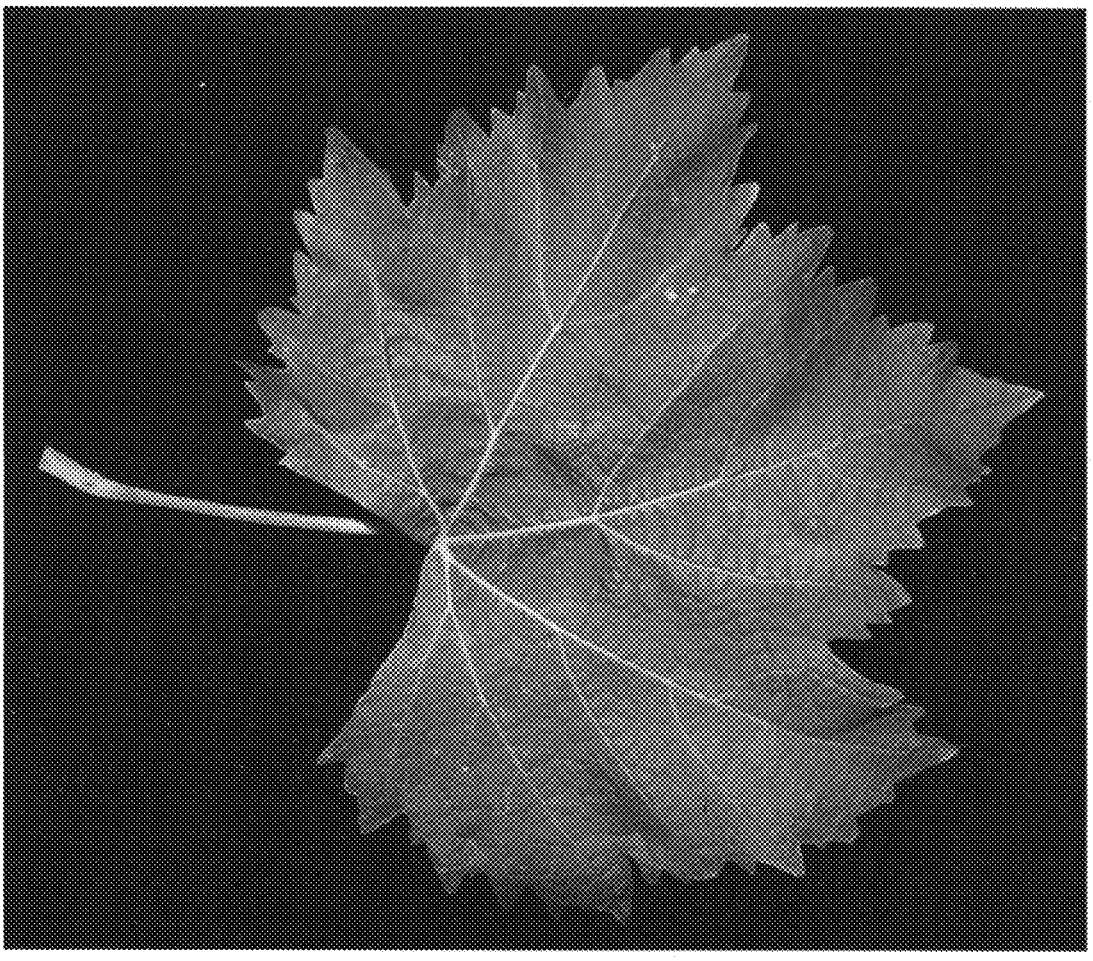
FIG. 2 is a photograph showing the leaf adaxial view.
Figure 3:
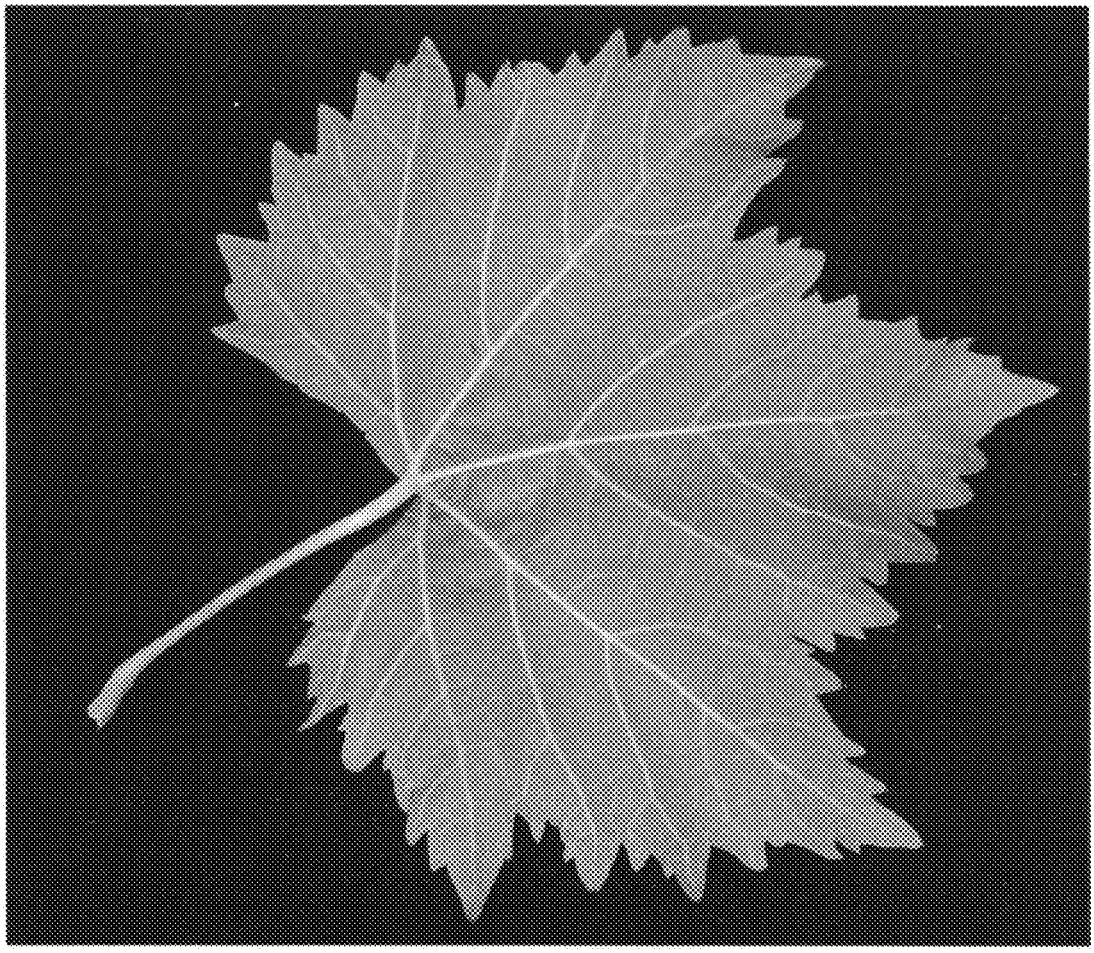
FIG. 3 is a photograph showing the leaf abaxial view.

'Gratitude' differs from its female parent A-1925 in that it is seedless and has green berry color compared to blue color for A-1925. 'Gratitude' differs from it male parent A-1581 as this parent is blue/black in fruit color, and has much smaller clusters.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. The data collection was from vines that were 15 years old.

Vine:

*Size*.—Medium.

*Growth*.—Moderately vigorous.

*Density of foliage*.—Medium.

*Productivity*.—Moderately productive.

*Rootstock*.—None; vines tested were own-rooted vines.

*Cold hardiness*.—Slight winter injury has occurred on the vines when winter lows of 5° F. occurred but injury was not seen at winter temperatures above this level.

*Shoots* (*current-season canes*).—Color of shoots on the side exposed to direct sunlight — Red-Purple Group (59A). Color on the side shaded from the sun Yellow-Green Group (146C). Anthocyanin present on the shoot sides exposed to direct sunlight. Shoot attitude is procumbent.

*Canes* (*mature measured in winter*).—Color of mature cane: base Greyed-Orange Group (165A); midpoint Greyed Orange Group (165A); terminal Greyed-Orange Group (165A); anthocyanin not observed on mature canes at base, midpoint, or terminal. Length average 2.5 m with range of 1.1 to 3.4 m. Diameter of mature cane: base 1.1 cm, midpoint 0.7 cm, terminal 0.3 cm. Internode length: base 4.7 cm, midpoint 7.5 cm, terminal 6.5 cm. Lenticels present and dense on mature canes and small (less than 0.5 mm in diameter). Canes mature to tips in the fall.

Trunk:

*Shape*.—Slender.

*Trunk straps*.—Long, split.

*Surface texture*.—Shaggy.

*Inner bark color*.—Greyed-Orange Group (166A).

*Outer bark color*.—Grey Group (201A).

Foliage:

*Leaves*.—Leaves simple and alternate; shape orbicular; number of lobes 1; petiole sinus shape open to half open; venation palmate; margin serrated with shape of teeth convex and teeth medium in size. Pubescence is sparse on mature leaves. Color of mature leaves: base abaxial — Yellow-Green Group (146B); base adaxial — Green Group (137B); midpoint abaxial — Yellow-Green Group (146B); midpoint adaxial — Green Group (137B); terminal abaxial — Yellow-Green Group (146B); terminal adaxial — Green Group (137B). Anthocyanin present lightly on the main and secondary veins. Color of young leaves: base abaxial — Yellow-Green Group (146C); base adaxial — Yellow-Green Group (146B); midpoint abaxial — Yellow-Green Group (146D); midpoint adaxial — Yellow-Green Group (146C); terminal abaxial — Yellow-Green Group (148D); terminal adaxial — Yellow-Green Group (146C).

*Petioles*.—Color on young leaves — Yellow-Green Group (146D). Color of mature petioles: abaxial side Yellow-Green Group (146D), adaxial side Greyed-Red Group (182B). Petiole anthocyanin present on the surface where it is most exposed to sunlight. Sinus of mature leaf is 4.9 cm deep and 6.0 cm at widest point. Mature leaves have sparse pubescence on midrib, main veins and secondary veins. Young leaves have medium pubescence on midrib, and sparse pubescence on main veins and secondary veins.

*Tendrils*.—Intermittent and opposite the leaf node. Length 25.8 cm. Texture smooth and usually forked and curled on distal end. Color of mature tendril Yellow-Green Group (146C).

*Buds*.—Average number of buds on a current, single-season cane 38. Dormant bud (compound bud or eye) width 3.4 mm; shape triangular and slightly rounded. Color Greyed-Orange Group (165A). Texture smooth.

Disease resistance: Moderately resistant to powdery mildew, and downy mildew; susceptible to black rot. Other disease or pest susceptibilities not known.

Flowers:

*Sex*.—Hermaphrodite.

*Date of bloom*.—May 11 (first); May 16 (full). Flowers per cluster — 341.

*Stamens*.—Number: 5. Color: Green-White Group (157D).

*Pistil*.—Number: 1. Length: 3.0 mm. Color: Yellow-Green Group (145A).

*Pollen*.—Color: Yellow Group (13C), normal and fertile. Petal — Cap of 5 fused petals, flat and round. Color — Yellow-Green group (147C).

*Sepal*.—None.

Fruit:

*Maturity*.—Late season August 19-28.

*Berry*.—Shape — Elongated oval. Color — Yellow-Green Group (146C). Size — Diameter at equator: 1.6 cm. Diameter at base: 1.4 cm. Diameter at apex: 1.3 cm. Length: 2.4 cm. Weight: 3.6 g; uniform in size. Texture — Non-slipskin. Skin thickness — Medium. Seeds — Seedless with 0 seeds per berry. Brush length — 5.48 mm. Flavor — Sweet, neutral flavor. Soluble solids — 16.2%.

*Juice*.—pH — 3.7. Titratable acidity — 2.7 g/L tartaric acid.

*Cluster*.—Weight — 516 g. Length — 14.8 cm. Width — 5.0 cm. Berries per cluster — 140-254, mean=207.4. Cluster per vine — 47.4. Clusters per shoot — One to two. Peduncle length — 1.91 cm. Pedicle: Length — 1.50 cm. Diameter — 0.12 cm. Color — Yellow-Green Group (146D). Use — Fresh consumption as a table grape is the primary use particularly for local markets. No processing evaluations done.

The cultivar: The most distinctive features of the cultivar are its seedless, crisp, green, thin-skinned berries with neutral flavor and resistance to fruit cracking from rainfall at maturity, large, tight clusters, medium vigor, and healthy plant.

We claim:

1. A new and distinct cultivar of grape plant named 'Gratitude' substantially as illustrated and described.

* * * * *